(12) United States Patent
Liu et al.

(10) Patent No.: US 10,274,443 B2
(45) Date of Patent: Apr. 30, 2019

(54) UREA CONCENTRATION IDENTIFICATION METHOD

(71) Applicant: Industrial Technology Research Institute, Hsinchu (TW)

(72) Inventors: Tzu-Yu Liu, Taichung (TW); Kuo-Chuang Chiu, Hsinchu (TW); Hung Tien, New Taipei (TW); Yeh-Chyang Huang, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 5 days.

(21) Appl. No.: 15/835,467

(22) Filed: Dec. 8, 2017

(65) Prior Publication Data

US 2018/0100820 A1 Apr. 12, 2018

Related U.S. Application Data

(62) Division of application No. 14/854,008, filed on Sep. 14, 2015, now abandoned.

(51) Int. Cl.
*G01N 27/02* (2006.01)
*G01N 33/18* (2006.01)

(52) U.S. Cl.
CPC ....... *G01N 27/026* (2013.01); *G01N 33/1886* (2013.01)

(58) Field of Classification Search
CPC . G01N 33/0036; G01N 33/0047; G01N 27/02
See application file for complete search history.

(56) References Cited

U.S. PATENT DOCUMENTS

| 2009/0266719 | A1 | 10/2009 | Hsiung et al. |
| 2014/0134067 | A1 | 5/2014 | Hartvigsen |
| 2014/0134607 | A1* | 5/2014 | Lin ............ G01N 27/327 435/5 |

FOREIGN PATENT DOCUMENTS

| CN | 1596826 | 3/2005 |
| CN | 101680378 | 3/2010 |
| CN | 102175742 | 9/2011 |
| CN | 102998342 | 3/2013 |
| TW | 201337256 | 9/2013 |
| WO | 0017385 | 3/2000 |

OTHER PUBLICATIONS

"Office Action of China Counterpart Application," dated May 30, 2018, p. 1-p. 7.

* cited by examiner

*Primary Examiner* — Devina Pillay
*Assistant Examiner* — Daniel P Malley, Jr.
(74) *Attorney, Agent, or Firm* — JCIPRNET (57) ABSTRACT

A urea concentration identification method is provided. By providing an identical sine-wave AC signal to each of the urea concentration identification devices placed in urea solutions of different concentrations, different impedance values are output by the urea concentration identification devices since the urea solutions of different concentrations have different electrical interactions with the electrodes of the urea concentration identification device. Differences of the impedance output by the urea concentration identification device function as a data set for determining the concentration of the urea solution to be determined.

10 Claims, 7 Drawing Sheets

UREA CONCENTRATION IDENTIFICATION METHOD

CROSS-REFERENCE TO RELATED APPLICATION

This application is a divisional application of and claims the priority benefit of U.S. application Ser. No. 14/854,008, filed on Sep. 14, 2015, now pending, which claims the priority benefit of Taiwan application no. 104113407, filed on Apr. 27, 2015. The entirety of each of the above-mentioned patent applications is hereby incorporated by reference herein and made a part of this specification.

TECHNICAL FIELD

The technical field relates to a urea concentration identification method.

BACKGROUND

Along with developments and applications of technologies, liquid concentration identification devices are needed in various fields, such as etchant formulation in a wafer manufacturing process or vehicle emission in an environment protection field.

Taking the vehicle emission for example, in order to comply with an environmental emission standard, heavy-duty diesel vehicles internationally tend to adopt a selective catalytic reduction (SCR) technique to reduce emissions of nitrogen oxide ($NO_x$) in exhaust gases. In detail, an SCR system includes a vehicle urea and an SCR device. The vehicle urea is injected into combusted exhaust gases from a urea tank and decomposes into ammonia ($NH_3$), such that a chemical reduction occurs to $NO_x$ by $NH_3$ in the SCR device to transform the $NO_x$ into nitrogen and water which cause no influence to the natural environment. Accordingly, the SCR system needs to consume a reactant (i.e., the vehicle urea) for normal operation. A vehicle urea solution is a solution of approximately 32.5% urea in water, where the concentration of the urea solution is strictly restricted, otherwise the $NO_x$ emission of a vehicle will exceed the standard and the SCR system of the vehicle may also be damaged.

SUMMARY

The disclosure introduces a urea concentration identification device and a method applied for identifying a concentration of urea. To measure the concentration of a urea solution, a sine-wave AC signal is applied to a urea concentration identification device. Since urea solutions of different concentrations have different electrical interactions with electrodes of the urea concentration identification device, if an identical sine-wave AC signal is provided to the urea concentration identification devices placed in urea solutions of different concentrations, different impedance values are output by the urea concentration identification device, and differences between the output impedance values are used as a reference for identifying the concentrations of the urea solutions.

The urea concentration identification device has a three-dimensional structure including a substrate, two electrodes and a dielectric layer that are stacked in the thickness direction, wherein a capacitor structure is formed on the substrate. The capacitor structure includes a circular lower electrode, a dielectric layer and a patterned upper electrode, wherein the patterned upper electrode provides an accommodating space for containing a solution, so as to increase the possibility as well as strength of electrical interaction between the urea solution and the electrode, for obtaining a spectrum of impedance characteristics.

Several embodiments accompanied with figures are described in detail below to further describe the disclosure in details.

DETAILED DESCRIPTION OF DISCLOSED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The term "coupling/coupled" used in this specification (including claims) may refer to any direct or indirect connection means. For example, "a first device is coupled to a second device" should be interpreted as "the first device is directly connected to the second device" or "the first device is indirectly connected to the second device through other devices or connection means." Moreover, wherever appropriate in the drawings and embodiments, elements/components/steps with the same reference numerals represent the same or similar parts. Elements/components/steps with the same reference numerals or names in different embodiments may be cross-referenced.

Terminologies used in the disclosure such as "first" and "second" used to describe each element, component, location, layer or section etc. should not be construed as limiting these elements, components, locations, layers or sections. These terminologies are merely used to differentiate between one element, component, location, layer or section, and another element, component, location, layer or section. Therefore, without departing from the teachings of the embodiments, the first element, component, location, layer or section referred in the disclosure below may also be referred as the second element, component, location, layer or section.

To facilitate description, spatially relative terms, such as "beneath", "below", "lower", "under", "above," "upper," "over" and the like, may be used herein for ease of description to describe one element or structural feature's relationship to another element(s) or structural feature(s) as illustrated in the drawings. It will be understood that the spatially relative terms are intended to encompass different orientations of the device in use or operation in addition to the orientation depicted in the drawings. For example, if the device in the drawings is turned over, elements described as "below" or "beneath" or "under" other elements or structural features would then be oriented "above" or "over" the other elements or structural features. Thus, the exemplary terms "below" and "under" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the disclosure. As used herein, the singular forms "a", "an" and "the" are intended to include the plural foil is as well, unless the context clearly indicates otherwise. It will be further understood that the terms "comprises" and/or "comprising," when used in this specification, specify the presence of stated structural features, integers, steps, operations, elements, and/or components, but do not preclude the presence or addition of one or more other structural features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Therefore, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

The disclosure introduces a urea concentration identification device and a method for performing urea concentration identification using the urea concentration identification device. Two embodiments will be illustrated as follows.

First Embodiment

Figure 1:
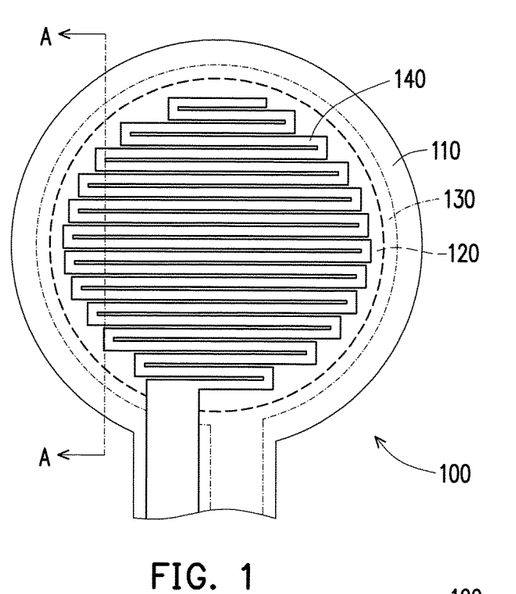
FIG. 1 is a schematic view of a urea concentration identification device according to a first embodiment.
Figure 2:
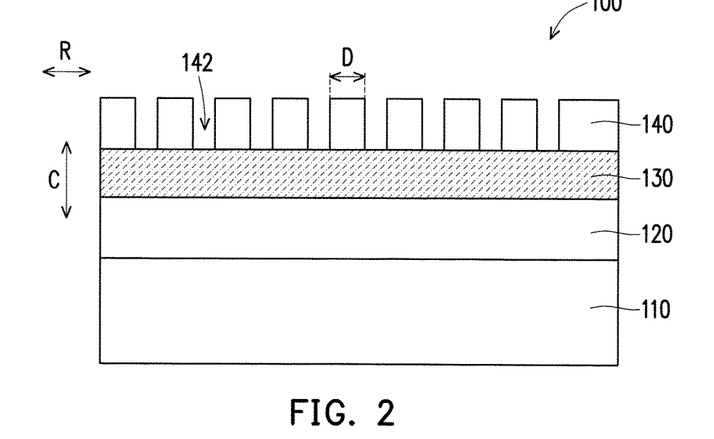
FIG. 2 is a cross-sectional view of the urea concentration identification device in FIG. 1 along section line A-A.

FIG. 1 is a schematic view of a urea concentration identification device according to a first embodiment. FIG. 2 is a cross-sectional view of the urea concentration identification device in FIG. 1 along section line A-A. Referring to FIG. 1 and FIG. 2 together, a urea concentration identification device 100 of the present embodiment is adapted to be placed in a urea solution for identifying a concentration of urea in the urea solution. This urea solution is a vehicle urea solution for use in an SCR system. The urea concentration identification device 100 includes a substrate 110; a lower electrode 120, disposed on the substrate 110 and having a substantially circular shape in a planar direction; a patterned upper electrode 140, disposed above the lower electrode 120; and a dielectric layer 130, disposed between the lower electrode 120 and the patterned upper electrode 140. The patterned upper electrode 140 includes a plurality of accommodating spaces 142, and a portion of the urea solution is contained in the accommodating spaces 142. The urea concentration identification device 100 has a three-dimensional capacitor C structure in a thickness direction, and a resistance R is generated in the planar direction.

Figure 3:
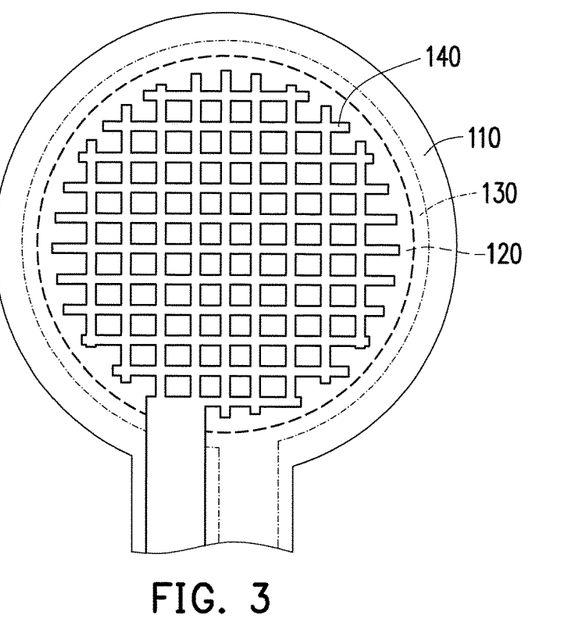
FIG. 3 is a schematic view of another pattern of a patterned upper electrode of the urea concentration identification device in FIG. 2.
Figure 4:
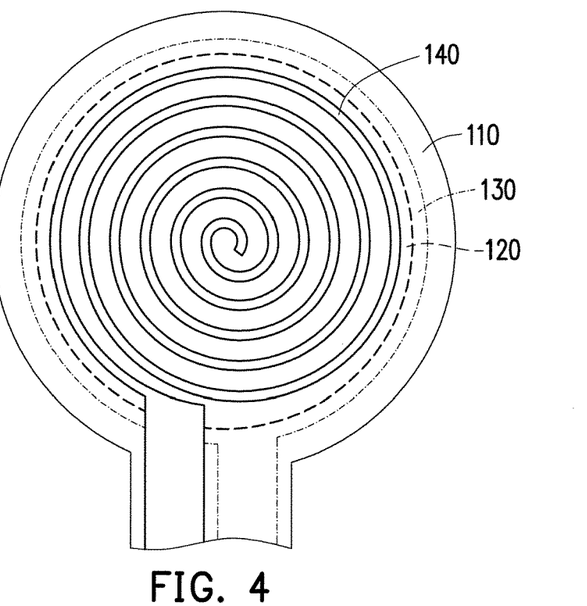
FIG. 4 is a schematic view of still another pattern of the patterned upper electrode of the urea concentration identification device in FIG. 2.

In the present embodiment, the substrate 110 is a substrate made of, e.g., but not limited to, ceramics. The substrate 110 may be made of any material having insulation properties, sufficient strength and urea corrosion resistance. A pattern of the patterned upper electrode 140 may be a meander line pattern (as shown in FIG. 1), a grid pattern (as shown in FIG. 3), a spiral pattern (as shown in FIG. 4) or any other pattern. Persons skilled in the art may select a pattern according to actual needs. The patterned upper electrode 140 has a linewidth in a range of, but not limited to, 50 μm to 500 μm. It is understood by persons skilled in the art that an identification resolution of the urea concentration identification device 100 may be adjusted by changing a linewidth D, line distance, thickness and area (not denoted) of the patterned upper electrode 140. Therefore, the linewidth, line distance, thickness and area of the patterned upper electrode 140 may be changed according to needs.

Figure 5:
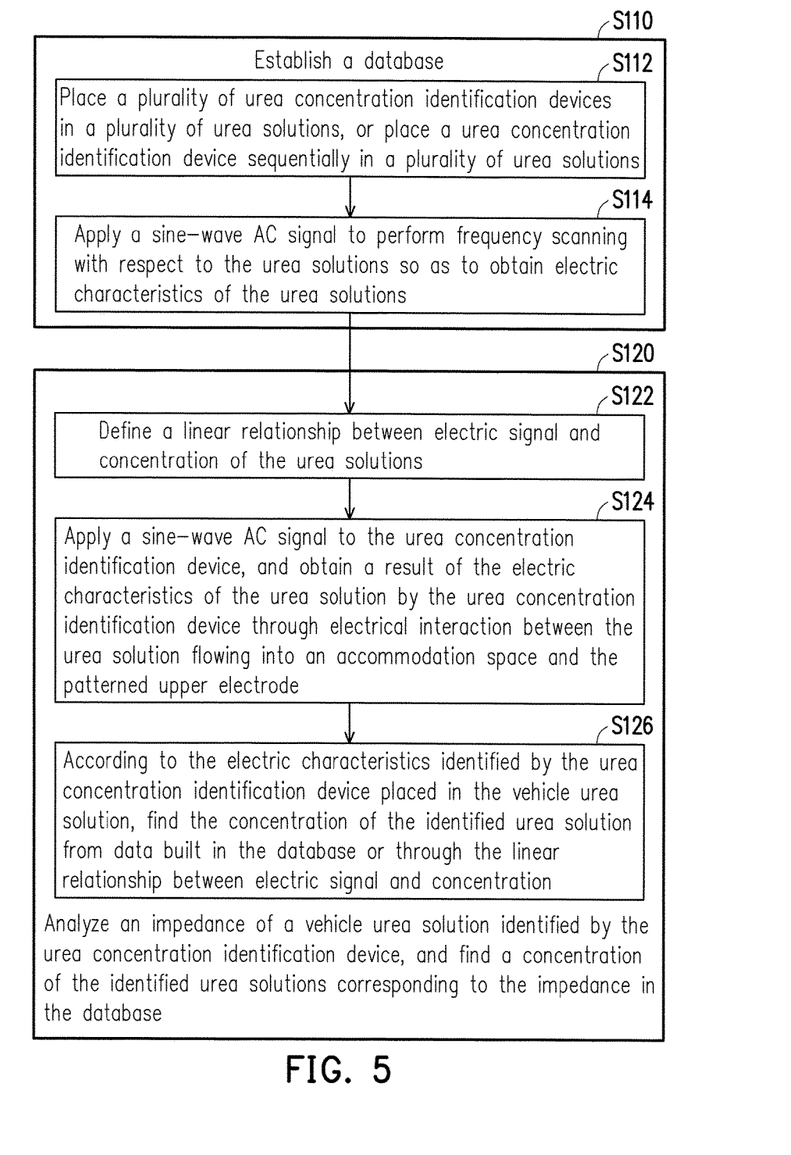
FIG. 5 is a flowchart illustrating steps of a method for performing urea concentration identification using the urea concentration identification device.
Figure 6:
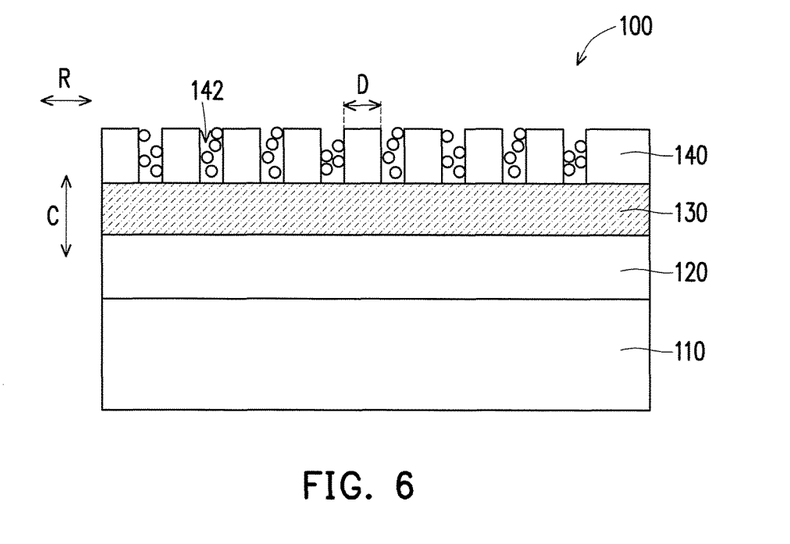
FIG. 6 is a schematic view illustrating that a portion of a urea solution flows into the accommodating space of the patterned upper electrode of the urea concentration identification device so as to be identified.

FIG. 5 is a flowchart illustrating steps of a method for performing urea concentration identification using the urea concentration identification device. Referring to FIG. 5, as shown in step S110, firstly, a database is established, wherein steps of establishing the database are as follows. As shown in step S112, a plurality of the urea concentration identification devices 100 are placed in a plurality of urea solutions, or the urea concentration identification device 100 is sequentially placed in a plurality of urea solutions for performing identification, wherein each urea concentration identification device 100 is electrically connected to an analysis unit (not illustrated) (e.g., a computer), so that a result identified by the urea concentration identification device 100 is transmitted to the analysis unit for analysis and storage of data. Moreover, each of the urea solutions to be identified has a different concentration. When the urea concentration identification device 100 is placed in the plurality of urea solutions, a portion of the urea solutions flows into the accommodating spaces 142 of the patterned upper electrode 140 (as shown in FIG. 6). Then, a sine-wave AC signal is provided to the urea concentration identification device 100. At this moment, the urea concentration identification device 100 is not placed in the vehicle urea solution in the SCR system, but in the urea solutions of predetermined concentrations that are deliberately formulated.

Figure 7:
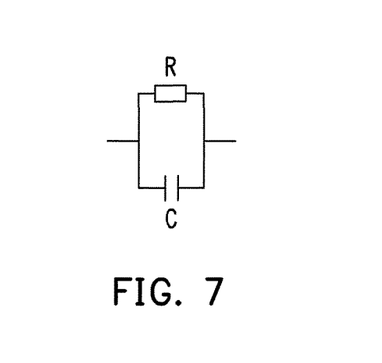
FIG. 7 is a schematic view of an RC parallel equivalent circuit generated during identification by the urea concentration identification device.

Next, as shown in step S114, frequency scanning is performed with respect to the urea solutions so as to obtain electric characteristics of the urea solutions. In detail, a sine-wave AC signal having a frequency ranging from $10^0$ to $10^6$ Hz is sequentially provided to the urea concentration identification device 100 in the urea solutions. Due to electrical interaction between the urea solutions flowing into the accommodating spaces 142 and the patterned upper electrode 140, an RC parallel equivalent circuit as shown in FIG. 7 is generated. Under different frequencies, the urea concentration identification device 100 obtains, and outputs through the lower electrode 120, different results of electric characteristics. The results of electric characteristics include, e.g., impedance, wherein the impedance includes information of a resistance R (denoted in FIG. 2) and a reactance, and the reactance may be an inductive reactance or a capacitive reactance. Step S114 is repeated so that frequency scanning is performed with respect to the urea solutions of different concentrations. Thus, different results of electric characteristics are output by the urea concentration identification device 100, and the obtained results are built in the database.

In addition, at the same time when the sine-wave AC signal is provided to the urea concentration identification device 100, a DC signal is further provided to the urea concentration identification device 100 so as to suppress noise.

Figure 8:
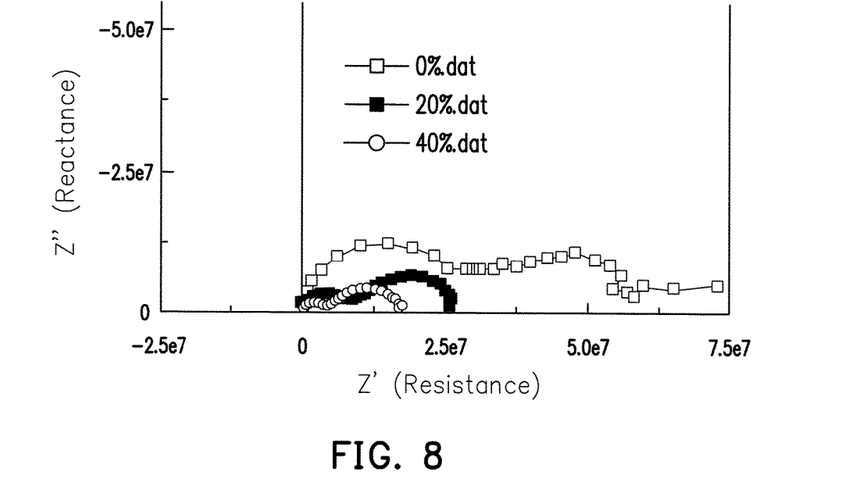
FIG. 8 illustrates the electric characteristics measured by the urea concentration identification device in urea solutions of different concentrations, wherein the horizontal axis indicates resistance and the vertical axis indicates reactance.

FIG. 8 illustrates the electric characteristics measured by the urea concentration identification device in urea solutions of different concentrations, wherein the horizontal axis indicates resistance and the vertical axis indicates reactance. Referring to FIG. 8, a relationship between reactance and resistance when the urea solutions have different concentrations (such as 0%, 20% and 40%) is illustrated. From FIG. 8, it is known that, due to the different concentrations of the urea solutions, the interaction between the urea solutions and the electrode has different strengths, and thus distributions of the electric characteristics of the urea solutions of different concentrations are distinguishable from each other.

By the above steps, the database has been established. Accordingly, when the urea concentration identification device 100 is applied in the SCR system, a result of electric characteristics corresponding to the concentration of the identified vehicle urea solution may be retrieved from the database.

To be more specific, the urea concentration identification device 100 is placed in the vehicle urea solution. As shown in step S120, an impedance of the vehicle urea solution identified by the urea concentration identification device 100 is analyzed, and a concentration of the identified urea solutions corresponding to the impedance is found in the database. In detail, the step of finding the concentration of the identified urea solutions corresponding to the impedance in the database includes step S122. A linear relationship between electric signal and concentration of the urea solutions of different concentrations is defined with reference to an impedance spectrum as shown in FIG. 8, wherein the linear relationship between electric signal and concentration is defined by selecting points that are more distinguishable (i.e., frequencies with respect to the reactance distribution of the urea solutions with different concentrations do not overlap with each other, or frequencies at which electric signals are distributed farther from each other). A reason for selecting the point that is more distinguishable to define the linear relationship is that the electric characteristics are more evident, thereby enabling a better concentration analysis.

Then, as shown in step S124, similarly to step S112, a sine-wave AC signal is applied to the urea concentration identification device 100. Due to electrical interaction between the urea solution flowing into the accommodating spaces 142 and the patterned upper electrode 140, a result of the electric characteristics of the urea solution is obtained by the urea concentration identification device 100. Next, as shown in step S126, according to the electric characteristics of the urea solution identified by the urea concentration identification device 100 placed in the vehicle urea solution, after calculation and analysis, the concentration of the identified urea solution is found from the data built in the database or through the linear relationship between electric signal and concentration.

From the above, it is known that the urea concentration identification device 100 of the present embodiment is fabricated to have a stacked structure in the thickness direction, which is different from some conventional urea concentration identification devices having an identification structure formed in the planar direction. Due to this structural difference, a contact area between the urea solution and the electrode is increased by the accommodating space 142 of the patterned upper electrode 140 for containing the urea solution, so that quality of identification is improved. In addition, through the establishment of the database and the definition of the linear relationship between electric signal and concentration, the concentration of the identified vehicle urea solution is easily retrieved from the identified result.

Second Embodiment

Figure 9:
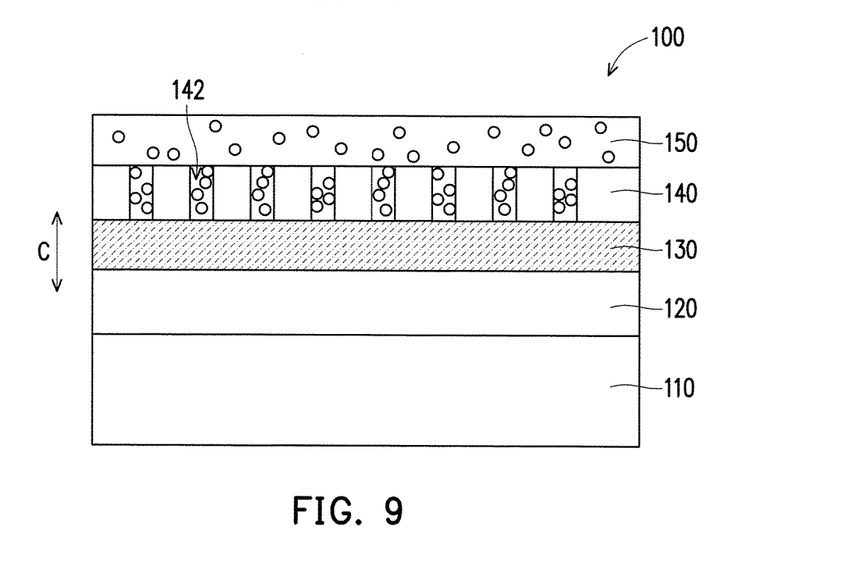
FIG. 9 is a schematic view of a urea concentration identification device according to a second embodiment.

FIG. 9 is a schematic view of a urea concentration identification device 100A according to a second embodiment. The present embodiment is roughly the same as the first embodiment. However, a difference lies in that the urea concentration identification device 100A according to the present embodiment further includes a porous layer 150 disposed above the patterned upper electrode 140, and the urea solution to be identified is adapted to enter the accommodating spaces 142 through the porous layer 150. A method of identifying the urea solution using the urea concentration identification device 100A according to the present embodiment is roughly the same as the identification method described in the first embodiment and is thus omitted.

Figure 10:
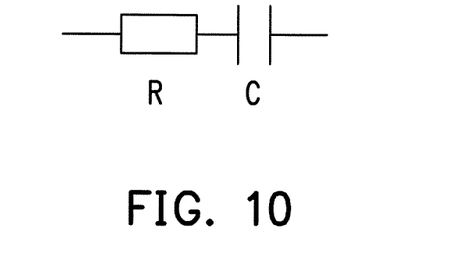
FIG. 10 is a schematic view of an RC series equivalent circuit generated during identification by the urea concentration identification device.

It is noted that by means of the porous layer 150 disposed above the patterned upper electrode 140, a microcavity is formed by the porous layer 150 and the patterned upper electrode 140. The urea solution is absorbed into the microcavity through the porous layer 150 to contact the electrode, so as to change a dielectric environment around the electrode, leading to a change in the impedance. Such structure generates, e.g., an RC series equivalent circuit (as shown in FIG. 10), and a signal difference between different urea concentrations is mainly attributed to capacitance.

Figure 11:
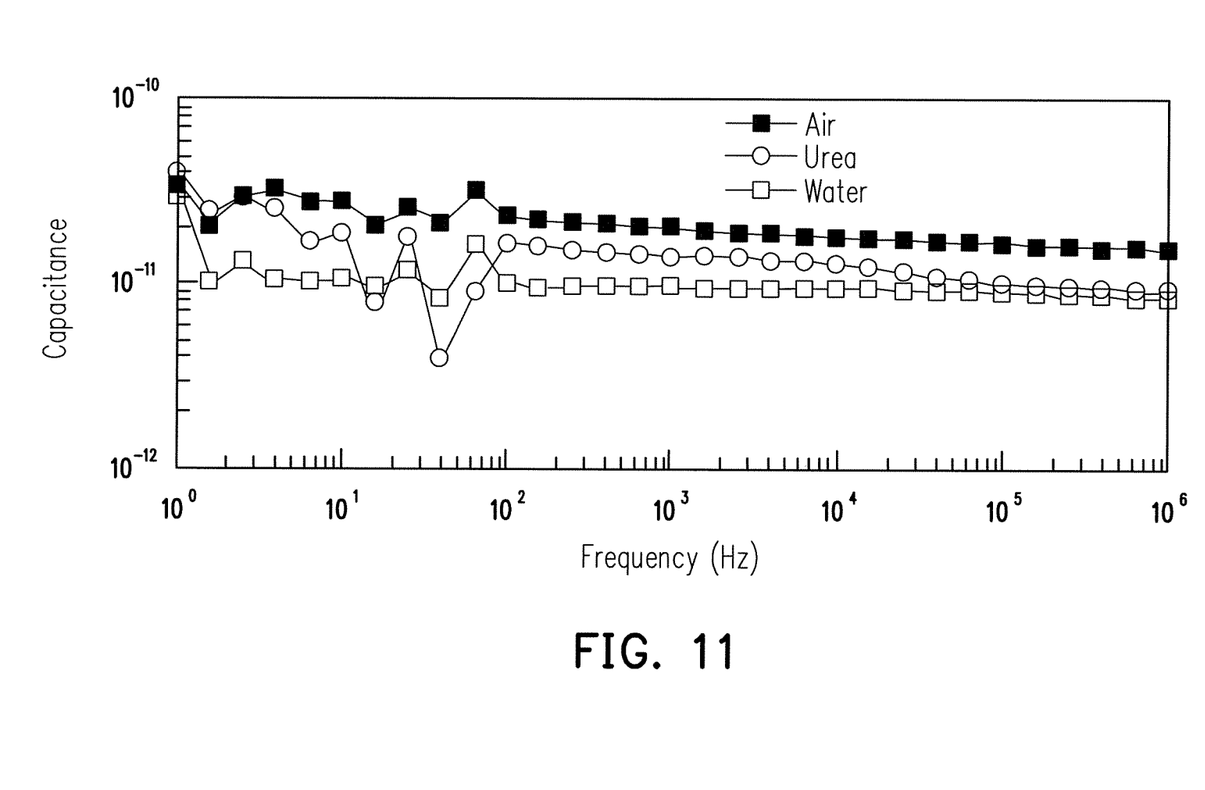
FIG. 11 illustrates a result of application of the urea concentration identification device according to the second embodiment to identification of different fluids.

In addition, the urea concentration identification devices 100 and 100A according to the first and the second embodiments may be applied to, not only urea solution, but also different fluids, as shown in FIG. 11. FIG. 11 illustrates a result of application of the urea concentration identification device 100A according to the second embodiment to identification of different fluids. The identified different fluids shown in FIG. 11 include, e.g., air, 40% urea, and water. Since each substance has its own electric characteristics, the different fluids have different electrical interactions with a device electrode, and thus different impedances are output. It will be apparent to persons skilled in the art, after understanding the content of this specification, that the concentration identification device of the disclosure may be used to identify not only concentration of urea but also concentration of other fluids (gases or liquids). The structure of the urea concentration identification device disclosed in the above embodiments is for use in a relatively simple identification environment (such as an environment where an object to be identified is a urea aqueous solution, air or fuel oil). In other relatively complicated identification environments, in order to avoid the possibility of signal overlap or interference caused by a plurality of substances in a solution, the structure of the concentration identification device may be modified according to needs, e.g., by a surface treatment of the electrode.

In summary, the urea concentration identification device and the urea identification method using the same according to the disclosure at least have the following advantages.

I. A urea concentration identification device different from some conventional structures is provided, wherein the urea concentration identification device has a three-dimensional capacitor structure including a substrate, an electrode and a dielectric layer stacked in the thickness direction, and thus a signal response rate is improved.

II. The accommodating space in the patterned upper electrode accommodates a portion of a solution to be identified, so that chances of electrical interaction between the solution to be identified and the electrode and strength of the electrical interaction are increased.

III. A porous layer is further disposed above the patterned upper electrode so as to form a microcavity to avoid external interference, so that identification accuracy is improved.

IV. By frequency scanning, an impedance characteristics spectrum of simultaneous measurement of a plurality of electric characteristics is obtained, and inaccuracy in the case of a single electrical response is avoided.

V. By adjusting the linewidth, line distance, thickness and area of the patterned upper electrode, an identification resolution of the urea concentration identification device is adjusted, so that excessively small impedance or unclear response is avoided.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A urea concentration identification method, comprising:
   providing a urea concentration identification device comprising a substrate, a lower electrode disposed on the substrate, a dielectric layer disposed on the lower electrode, and a patterned upper electrode disposed on the dielectric layer, wherein the patterned upper electrode comprises a plurality of accommodating spaces, and placing the urea concentration identification device in a urea solution to be identified, wherein a portion of the urea solution enters the accommodating spaces of the patterned upper electrode of the urea concentration identification device;
   providing a sine-wave AC signal to the urea concentration identification device, so that the urea solution in the accommodating spaces electrically interacts with the patterned upper electrode, and the urea concentration identification device identifies an impedance; and
   analyzing the impedance identified by the urea concentration identification device, and retrieving from a database a concentration of the identified urea solution corresponding to the impedance.

2. The urea concentration identification method of claim 1, further comprising providing a DC signal to the urea concentration identification device concurrently with providing the sine-wave AC signal to the urea concentration identification device, so as to suppress noise.

3. The urea concentration identification method of claim 1, wherein steps of establishing the database comprise:
   placing the urea concentration identification device in the urea solution of different concentrations, and providing the sine-wave AC signal to the urea concentration identification device; and
   performing frequency scanning with respect to the urea solution so as to obtain an impedance spectrum, and recording the impedance spectrum in the database.

4. The urea concentration identification method, of claim 3, wherein the step of retrieving the concentration of the identified urea solution from the database corresponding to the impedance comprises:
   defining a linear relationship between electric signal and concentration of the urea solution of different concentrations according to the impedance spectrum; and
   finding the concentration of the identified urea solution through the linear relationship between electric signal and concentration according to electric characteristics of the identified urea solution identified by the urea concentration identification device.

5. The urea concentration identification method of claim 1, wherein the impedance output by the urea concentration identification device comprises a resistance and a reactance.

6. The urea concentration identification method of claim 5, wherein the reactance is an inductive reactance or a capacitive reactance.

7. The urea concentration identification method of claim 1, wherein the substrate comprises a ceramic substrate.

8. The urea concentration identification method of claim 1, further comprising forming a grid pattern, a spiral pattern or a meander line pattern on an upper electrode disposed on the dielectric layer to form the patterned upper electrode.

9. The urea concentration identification method of claim 1, wherein the patterned upper electrode has a linewidth ranging from 50 μm to 500 μm.

10. The urea concentration identification method of claim 1, further comprising disposing a porous layer above the patterned upper electrode, wherein the urea solution to be identified is adapted to enter the accommodating spaces through the porous layer.

* * * * *